United States Patent [19]
Chang

[11] Patent Number: 5,734,459
[45] Date of Patent: Mar. 31, 1998

[54] ANOMALOSCOPE WHICH CAN GENERATE DIFFERENT ILLUMINANCES FOR TEST

[75] Inventor: Yin Chang, Taipei, Taiwan

[73] Assignee: National Science Council, Taipei, Taiwan

[21] Appl. No.: 613,996

[22] Filed: Mar. 11, 1996

[51] Int. Cl.$^6$ ................................................ A61B 3/06
[52] U.S. Cl. .................................... 351/242; 351/237
[58] Field of Search ................................ 351/222, 243, 351/237, 221, 220

[56] References Cited

U.S. PATENT DOCUMENTS

| | | | |
|---|---|---|---|
| 4,798,458 | 1/1989 | Gehrung et al. | 351/242 |
| 4,966,453 | 10/1990 | Chang et al. | 351/242 |

FOREIGN PATENT DOCUMENTS

| | | | |
|---|---|---|---|
| 1735230 | 2/1994 | Japan | . |
| 36290 | 1/1990 | Taiwan | . |

OTHER PUBLICATIONS

Alpern, et al., Visual Pigment Kinetics in Abnormalities of the Uvea–Retinal Epithelium Interface in Man, Invest. Ophthalmal and Vis. Sci. 20, 183–203, 1979.

Wald, Molecular Basis of Visual Excitation, Science, 162, 230–239, 1968.

Penn, et al., Signal Transmission Along Retinal Rods and the Origin of the Electroretinographic α–Wave, Nature 223, 201–205, 1969.

Stryer, Cyclic GMP Cascade of Vision, Annu. Rev. Neurosc. 9, 87–119, 1986.

Pugh, et al., Visual Transduction in Vertebrate Rods and Cones: A tale of Two Transmitters, Calcium and Cyclic GMP., Vision Rev. 26(10), 1613–1643, 1986.

Fung, Transducin: Structure, Function and Role in Phototransduction, Progress in Retinal Research, Chap.6, Persimmon Press, Oxford 1987.

*Primary Examiner*—Huy Mai
*Attorney, Agent, or Firm*—Beveridge, DeGrandi, Weilacher & Young, L.L.P.

[57] ABSTRACT

In this device, we employed four sets (or three sets) of different wavelength light sources and mixed each other to form the Moreland's color matching equation (a 580 nm+b 480 nm=c 440 nm+d 500 nm) or the Rayleigh's color matching equation (a 590 nm=b 546 nm+c 650 nm) and resulted in two mixed lights. On these two light paths, we employed a flat mirror to separate them into two halves and formed a single light path. On this light path, we added a neutral density filter to adjust light intensity to reach our purpose of attenuating the light intensity. In addition to this, a shutter diaphragm was set on the same light path to adjust a proper lighting area on the retina. Behind the shutter diaphragm, a set of lenses focused the light beam on to the observer's pupil of human. In order to monitor the observer's eye of human, a set of IR LED's was put and surrounded the transmission hole of the housing in front of the observer's eye, and the reflective IR light of the eye image was reflected by a dichroic mirror which was aligned 45 degrees with the impinging light beam and caused the eye image being caught by a CCD camera. Thus the eye image could be monitored by a B/W TV and the focused light position on the pupil could be adjusted.

17 Claims, 12 Drawing Sheets

ANOMALOSCOPE WHICH CAN GENERATE DIFFERENT ILLUMINANCES FOR TEST

FIELD OF THE INVENTION

The present invention relates to an anomaloscope for generating different illuminances for test and, in particular the said anomaloscope employed optical and electronic devices with the control of software in order to achieve the Moreland's matching or Rayleigh's matching equation.

BACKGROUND OF THE INVENTION

Description Related to Prior Art

When light beam illuminated on the retina through cornea, pupil, lens and vitreous body, molecules of photopigment of the photoreceptors on the retina excited by this light beam will be deformed and hence, generate a current flow as illustrated by Wald G. in his literature in 1968—Molecular basis of Visual Excitation. Science 262, 230–239, and by Penn R. D. et al in their literature in 1969—Signal Transmission along retinal rod and the Origin of the Electroretinographic a-wave. Nature 223, 201–205. This deformed molecules of photopigment will be no longer in possession of its original character to accept light excitation and therefore, requires a period of time plus a series of chemical reactions before to be recovered to its origin, such as described in an article written by Stryer L—Cyclic GMP cascade of Vision. Annu. Rev. Neurosc. 9, 87–119, 1986—or, by Pugh E. N. et al.—Visual transduction in Vertebrate rods and cones, Vision Res. 26(10), 1613–1643, 1986—and by Fung, B. K. K.—Transducin: structure, function and the role in phototransduction. In "progress in retinal research" chap. 6, Persimmon Press, Oxford 1987. Alpern, MA & Krantz, DH-visual pigment kinetics in abnormalities of the uvea-retinal epithelium interface in man, Invest. Ophthalmal and Vis. Sci. 20, 183, 1979.

For the ordinary person, after the photoreceptor was excited by different light intensity by a period of time, the deformed molecules of photopigment thereon may return to its original form. The average capability of its recovery shall be effected by the micro-environment and this is what we called "metabolic activity". Based on the study made by Alpern MA et. al. ("Visual Pigment kinetics in abnormalities of the uvea-retinal epithelium interface in Man", Invest Ophthalmic and Vis Sci, 20: 83, 1979) the retinal pigment epithelium is one of the most active areas on the human body in metabolism. Apparently, under some conditions, the influence of this metabolic activity will lead the observer to have different color match under different brightness of light beam. This difference shall also appeared on the observer's retina, which accordingly, indicated whether its metabolic activity is normal or abnormal.

However, the micro-environment during the course of its recovery undertake by these molecules somehow will effect the rate thereof. That is to say; if the strength of light increases, the amount of deformed photopigment molecules needed to be recovered will correspondingly increase. To speak as a whole, the metabolic activity effected by this micro-environment is bound to have a change. Consequently, sensitivity to color change for a person under test shall also be changed accordingly, so is the difference of color matching caused by this change occurred. The stronger the light applied to retina, the great the difference-in Color matching appeared from the person under test whose metabolic activity is abnormal. This is because we usually are unable to take a direct measurement to the rate of metabolism on the bottom portion of human eye, but to re-laid on a method of measurement which can provide an indirect way to indicate its metabolism.

So far as we know, there are the following patent priorities proposed to use methods of color matching such as Moreland's match or Rayleigh match to identify the anomalous color vision of a person taking the test: ROC Patent No. 36290—Four Light Channel anomaloscope-, Japanese Patent No. 1735230, and U.S. Pat. No. 4,966,453. However, the principle used by the present invention is completely different from the above three patent priorities and is more delicate in construction and novel in designing. The greatest difference is that the present invention can detect the dynamic change of the photopigment density along with the changing retinal illuminances This is also the first one to use a TV monitor to directly reflect the observer's eyeball image during the course of test in comparison with U.S. Pat. No. 4,966,453. The anomaloscope of the present invention can produce more uniform project light than that of the above U.S. patent.

SUMMARY OF THE INVENTION

In view of the above, the major objective of the present invention is to provide an anomaloscope, which employed four sets(or three sets) of different wavelength light sources and mixed each other to form the Moreland's color match or Rayleigh's color match, and also employed a flat mirror to separate them into two halves in two different mixed light paths of different wavelength and form a mixed light of different color at both right and left sides of same light path.

The further objective of the present invention is to provide an anomaloscope which added optical and electronic devices with software control means in the system so as to achieve Moreland's color matching equation or Raleigh's color matching equation, and also provide color matching at different illuminance for test.

Still another object of the present invention is to test the retina portion, especially the dynamic change of photopigment of its photoreceptor, under the excitation of light beam of different strength while placed in different illuminance, whether abnormal metabolism existed among its cells. Thus, an indirect way of method is provided for measuring human metabolic activity.

In order to achieve the above objectives, a four channel anomaloscope which can generate different illuminance for test of the present invention, similar to those known anomaloscopes, included a housing, optical device, circuit control means, computer with software programs, illuminating light bulb, interference filter of single wavelength, lens, 50/50 beam splitter, reflector, photodiodes, flat mirror, and CCD camera. In addition to the above, the present invention also includes a hot mirror h.m., a neutral density filter, diaphragm, dichroic mirror and biconcave lens.

The anomaloscope of the present invention employed four sets(or three sets) of different wavelength light sources and mixed each other to form the Moreland's match or Rayleigh's match and resulted in two mixed lights. On these two light paths, we employed a flat mirror to separate them into two halves and formed a single light path. On this light path, we added a neutral density filter to adjust the light intensity to reach our purpose of attenuating the light intensity. In addition to this, a shutter diaphragm was set on the same light path to adjust a proper lighting area on the retina of the person. Behind the shutter diaphragm, a set of lenses focused the light beam onto the observer's pupil that will form a Maxwilliam view for the observer. In order to monitor the observer's eye, a set of IR LEDs was put and surrounded in front of the observer's eye, and the reflective IR light of the eye image was reflected by a dichroic mirror which was aligned 45 degrees with the impinging light beam and caused the eye image being caught by a CCD camera in order to obtaining a corresponding adjustment.

Other objectives, features and advantages of the present invention will become apparent upon consideration of the following detailed description and the accompanying drawings, in which:

DETAILED DESCRIPTION

Figure 1:
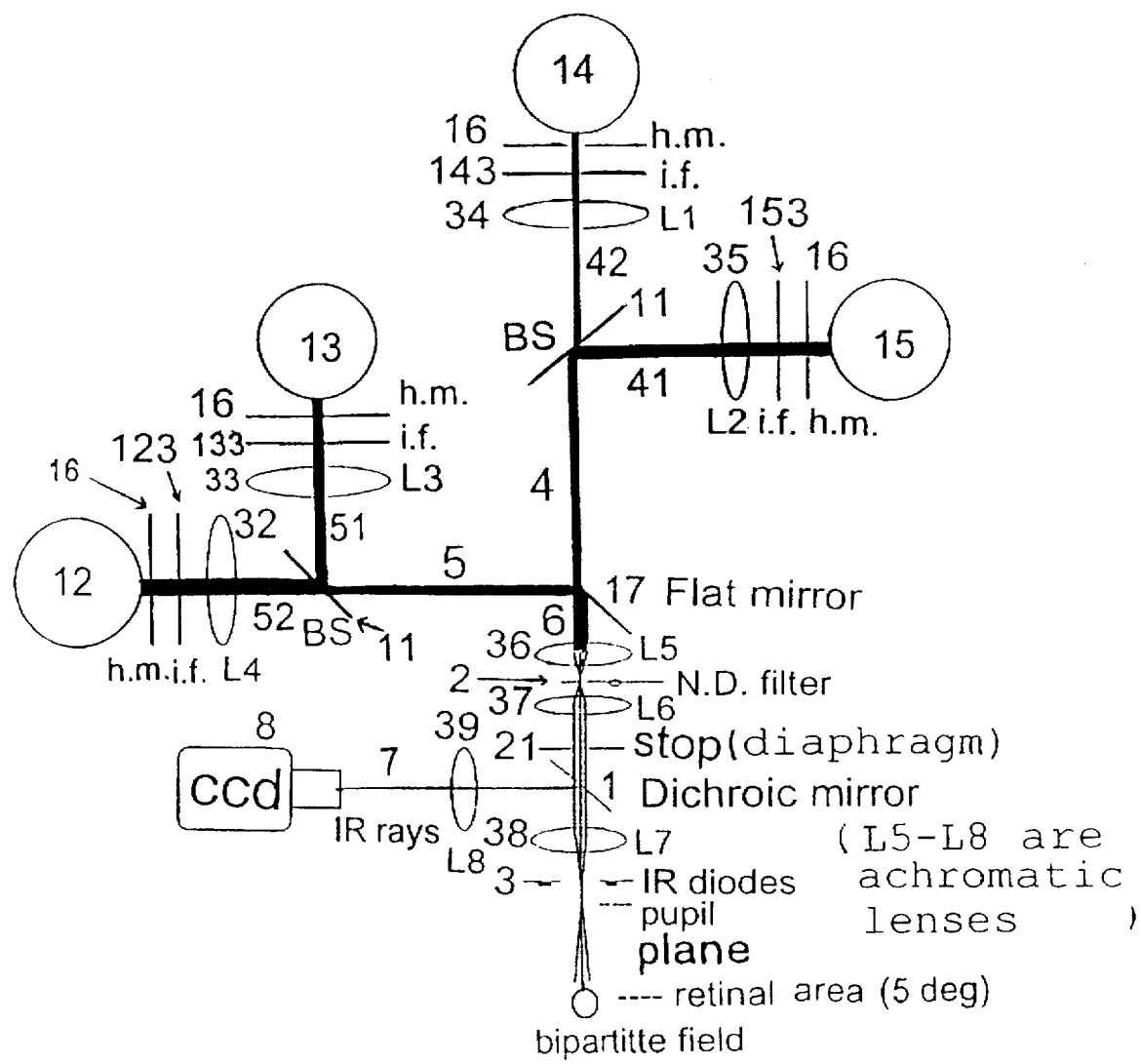
FIG. 1 is a schematic diagram showing the structure of a four channel anomaloscope which can generate different illuminance for test according to the present invention.
Figure 2:
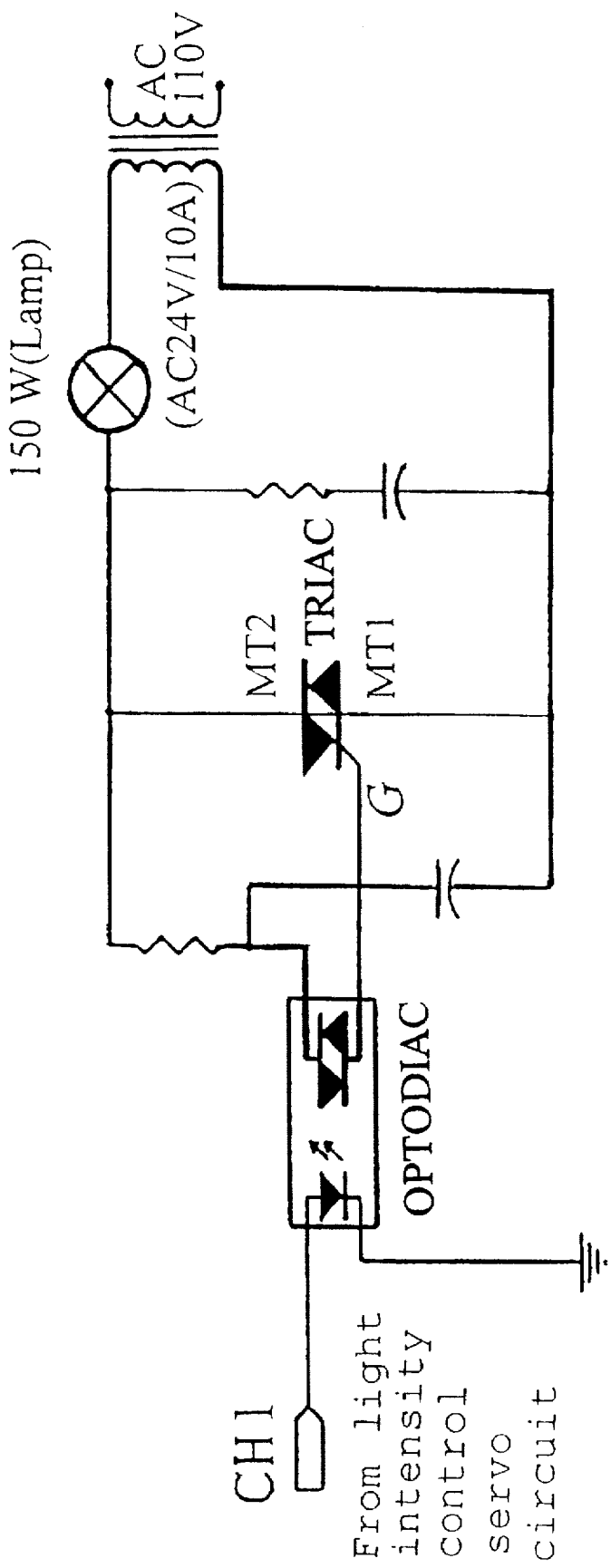
FIGS. 2 to 5 are diagrams showing circuit control means to be used in the system of FIG. 1.
Figure 3:
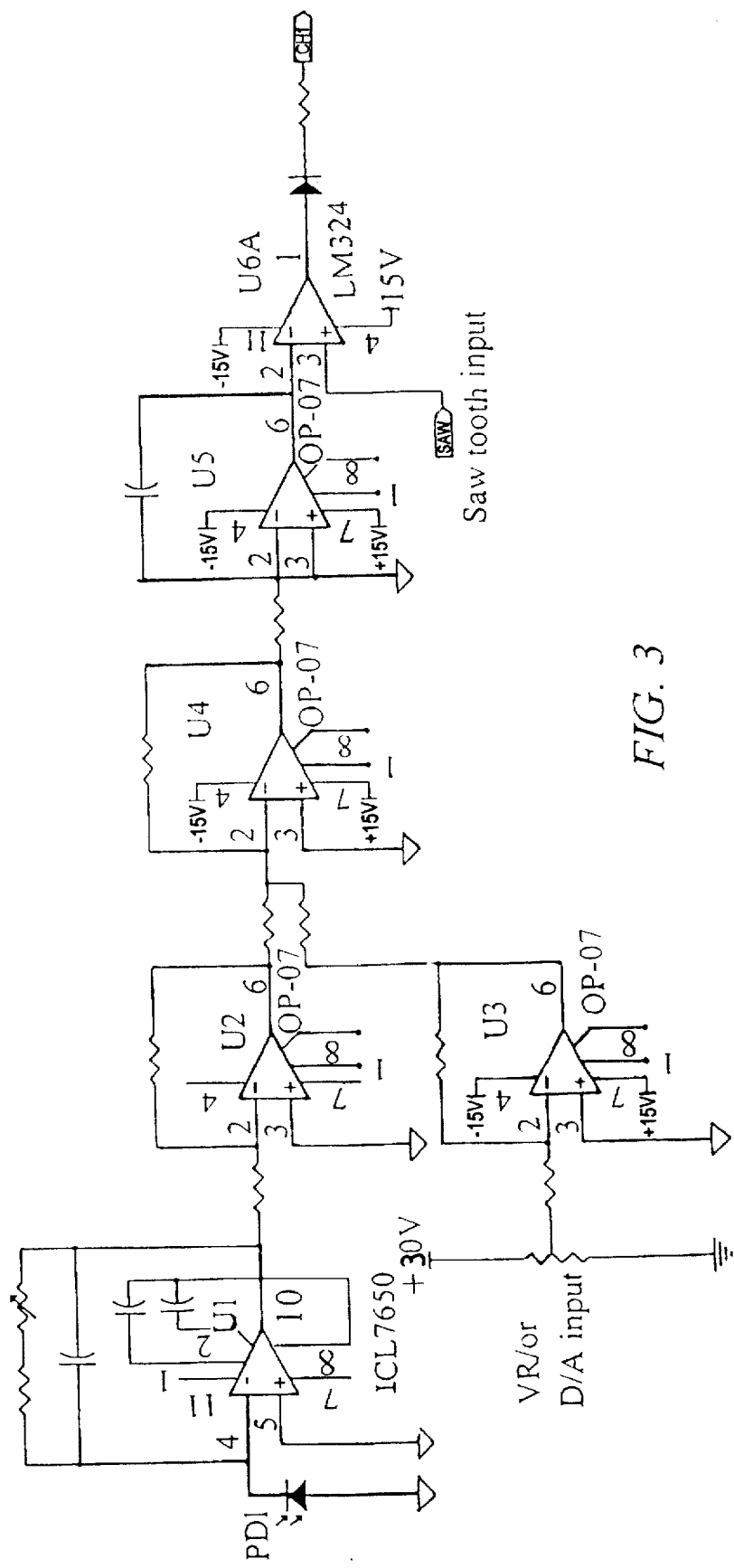
Figure 4:
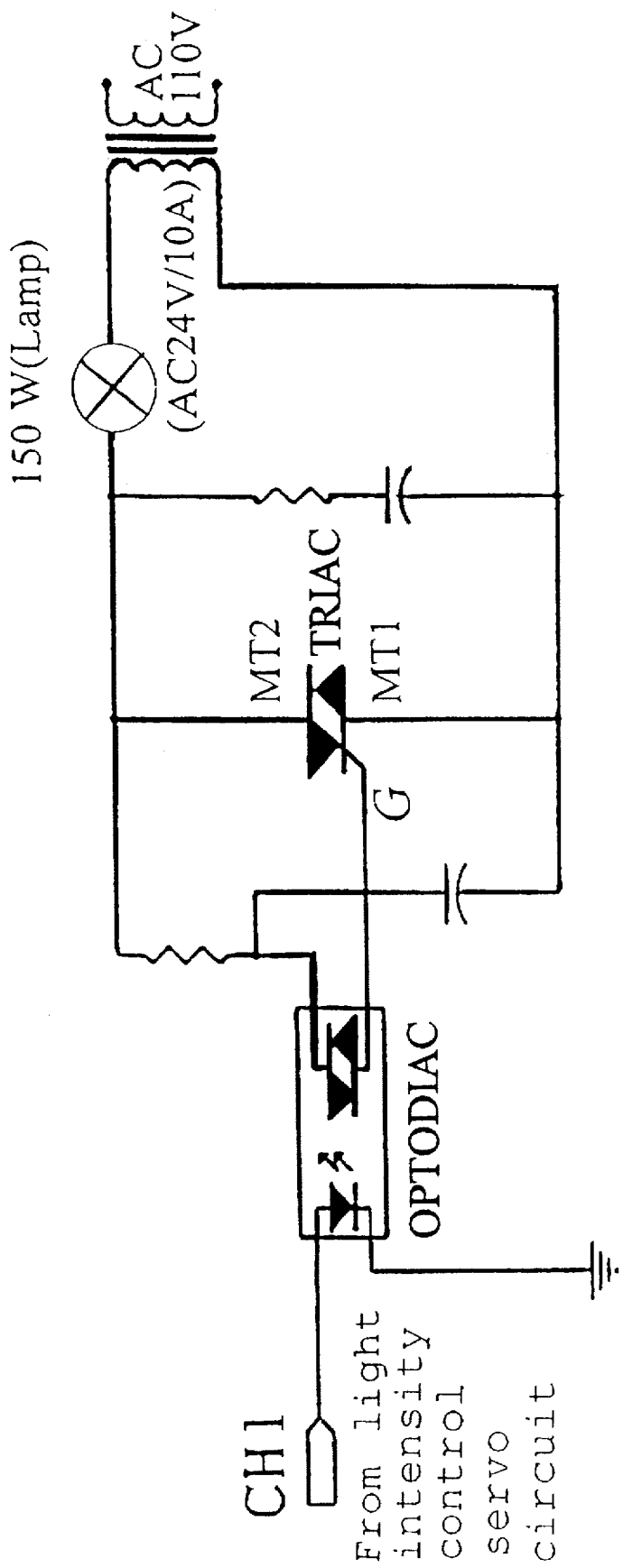
Figure 5:
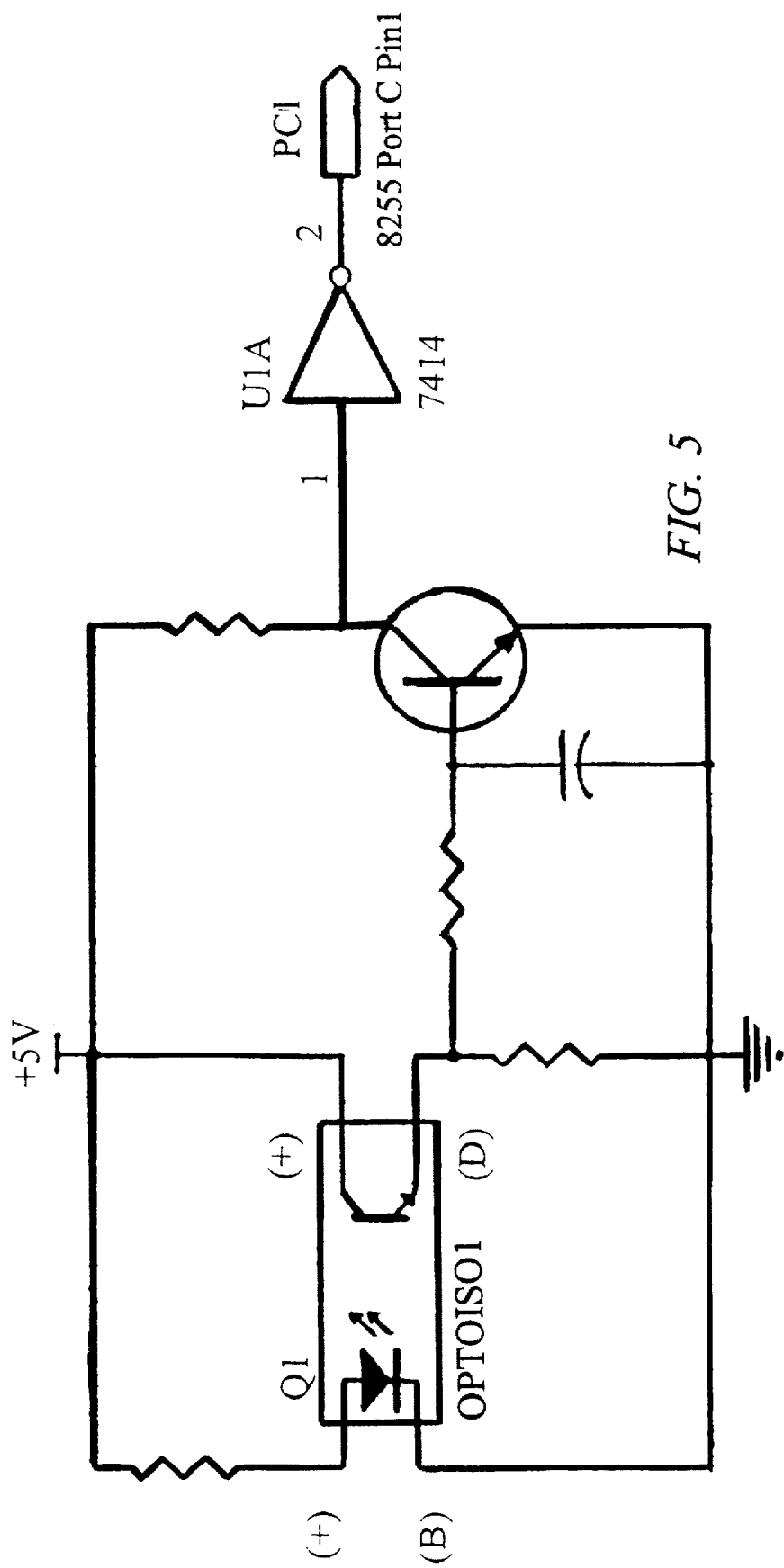

Refer to a four channel anomaloscope which can generate different illuminance for test according to the present invention as illustrated in FIG. 1, which includes: a housing, optical device, circuits control means, computer with software programs, illuminating light bulb, interference filter of single wavelength, hot mirror (h.m.), lens, 50/50 beam splitter, reflector, photodiodes, neutral density filter, diaphragm, transmission device, dichroic mirror and CCD camera.

The construction of a four channel anomaloscope which can generate different illuminance for test according to the present invention are such:

The housing is similar to that of the conventional ones;

Its optical device is placed inside of the housing;

Its circuit control means as illustrated in FIGS. 2 to 5 are connected to optical device for controlling the operation of the same; and computer with software programs is adopted to cooperate with circuit control means for precisely controlling the operation of said optical device;

In which,

The inside of the housing has been divided into upper and lower chambers by a ventilate partition plate and light transmission holes are provided on lateral side of said upper chamber. A plurality of small holes are provided on the top wall of the housing for heat spread. The upper chamber is for accommodating all optical devices such as a plurality of illuminating light bulbs and a plurality of hot mirrors;

These hot mirrors are located adjacent to a respective light bulb and reflect the portion of IR light emitted from light bulb back into the lamp housing of each bulb. Heat produced inside of this housing will be blow-out by fans located at the bottom of this chamber.

A plurality of interference filters of single wavelength are mounted at a location close to respective light bulb for limiting the light which emitted from each bulb into different light beams of single wavelength;

A plurality of lens are employed respectively on light paths of different wavelength with a focus length just equal to a distance between each lens and lamp filament;

A plurality of 50/50 light splitters mounted respectively on the crosspoints of two light beams of different wavelength and mix each other of said two light beams of different light paths;

Reflector is used to reflect the light beam which was mixed by light splitter and let the mixed light reflect through a transmission hole on the housing and constituted two halves; and A plurality of photodiodes are mounted at the rear side of interference filter and adopted to receive the strength of lights of different wavelength so as to achieve the purpose of negative feedback automatical control.

A plurality of achromatic lenses respectively located on the light paths of two halves mixed light; In which, a single achromatic lens will focus this two halves mixed light onto a ND filter of round shape.

ND filter is a circular non-linear type and its maximum attenuation capability to light intensity is $10^4$ times and its angular turning will be controlled by a "ONE STEP MOTOR", so that, light beam passes through locations of different transitivity to achieve the purpose of attenuation.

On the other side of ND filter, at the point of equal focus length, employed an achromatic lens, on the light path behind this achromatic lens employed a shutter diaphragm with its diameter being adjustable for adjusting the size of diameter of this two halves light beam. Next to this diaphragm, a dichroic mirror was set in 45 degrees on the light path. Behind this dichroic mirror another achromatic lens is adopted to focus the mixed light beam to a point exceeding a certain distance which would be the center of pupil of person under test. In the surrounding area of transmission holes(on the face plate of housing) on the light path within focus length of said achromatic lens, four IR LEDs were set to illuminate the subject's eye and the reflected light from observer's pupil passing through the achromatic lens in front of eyeball to the above mentioned dichroic mirror which is in a position of 45 degrees from the light path. This light, after reflection by the dichroic mirror, shall pass through another achromatic lens and caused the eye image being caught by a CCD camera.

The structure of the four channel anomaloscope which can generate different illuminance for test according to the present invention as shown in FIG. 1, employed four sets of light sources which are all halogen lamps placed inside of a respective lamp housing of cylinder in shape and its lights are passing through round holes (12–15) to generate single color light beams when it reach to hot mirror (16) and filters (i.f. 123, 133, 143, 153) of specific wavelength. When these single color lights are passing through lenses (32–35) with the focus of these lenses positioned on the lamp's filament, these divergent light beams will become parallel beams and gather onto beam splitter together with another beam of single color in right angle with these parallel beams which resulted in a mixed light of two single color. Behind each filter (i.f. 123, 133, 143, 153) we employed a photodiode (3) to detect the strength of light beam passing through this channel in order to keep a constant of light intensity at each half of the bipantite field during a test. This can be achieved by a negative feedback circuit under a computer control program.

When two sets of mixed lights (4,5) each was mixed by two light beams in right angle with each other, (41,42,51, 52), reached to the edge of a flat mirror (11) which is facing a direction of 45 degrees to respective light beams, a portion of mixed light (51,52) will be reflected in right angle into an achromatic lens (36) of short focus length which is capable to eliminating color difference of a image. The other portion of mixed light (41,42) directly goes into the achromatic lens (36), since these two sets of mixed light are all parallel light, a part of these mixed light shall be blocked by this flat mirror. Having passed through achromatic lens (36), all the lights are focused on a circular ND filter. This circular ND filter (2) covered an attenuating range of $10^4$ times of light intensity. Its attenuation rate is controlled by a step motor. Through position adjustment, this attenuation can be repeated precisely at eight points which required to attenuating the light intensity, thus, an uniformed light intensity for test can be obtained.

Achromatic lenses (36,37) focus lights on the ND filter (2). Hence, through which the said two sets of mixed light (6) appeared to be in the form of parallel light. The diaphragm (21) on this light path(6) can adjust its size of diameter in order to bring the two halves of mixed light (6) to be appeared on the retina with a range from 0 degree to 15 degree of visual field, and set the 2 degree, 5 degree and 10 degree as major targets. This parallel light will pass through a 45 degrees positioned dichoric mirror (1), which can reflect IR light and allows visible light passing through, and entered into another achromatic lens (38). Since the achromatic lens (38) has comparatively a longer focal length, it brings the lamp filament images of the forementioned four light sources to the center of observer's pupil and form a confocal image. Again, this image will form a Maxwilliam view on the retina and, that shall be able to make these two halve circles appeared on the observer's retina as a color circle with uniform brightness. In addition, four infrared light emitted diodes (3,IR LEDS) are set around the transmission hole in front of the test subject's eye to illuminate the test subject's eyeball, and the reflective IR light of the eye image is reflected by a dichroic mirror (1) which is on the light path and causes the eye image being caught by a CCD camera through an achromatic lens (39). Thus the eye image can be monitored by a B/W TV. The movement of observer's eyeball and the alignment of pupil's position are well under control so as to achieve the best adjustment for focusing light position on the pupil.

An anomaloscope which can generate different illuminance for test according to the present invention is thus constructed the middle plate at the internal of housing has a plurality of air holes at the same height with light bulbs having a diameter between 1 and 1.5 cm. Four air fans for spreading heat are mounted respectively at the bottom of each lamp housing. The preferable light bulbs are FCS 24V, 150 W-series of GE products or equivalent projection lamp. Number of light bulbs to be used should be more than one and four is most preferable and so is the number of hot mirrors which is variable accordingly.

Figure 6:
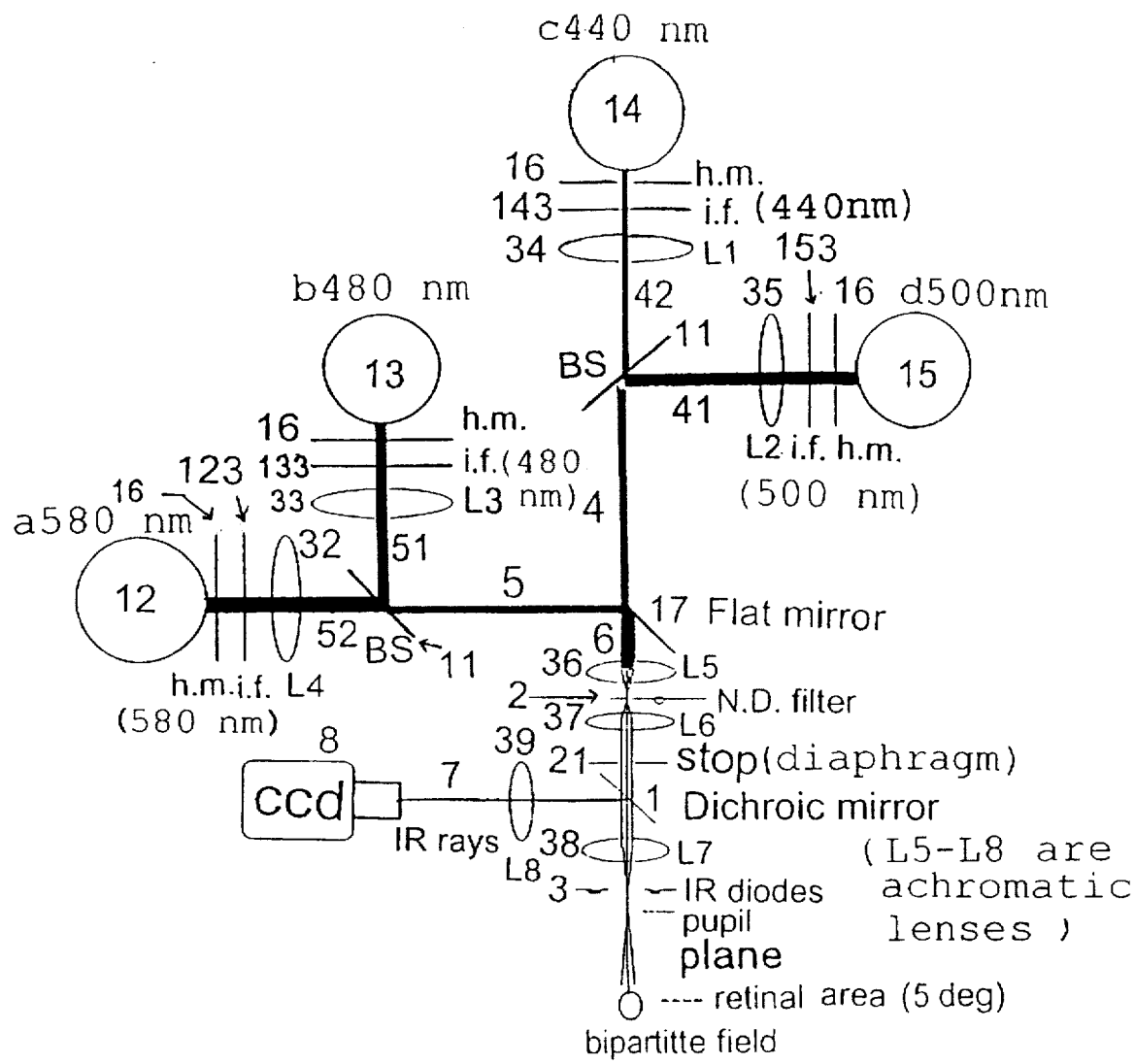
FIG. 6 is a schematic diagram showing one of the embodiment of a four channel anomaloscope which can generate different illuminance for test, in which, Moreland match is being used.
Figure 7:
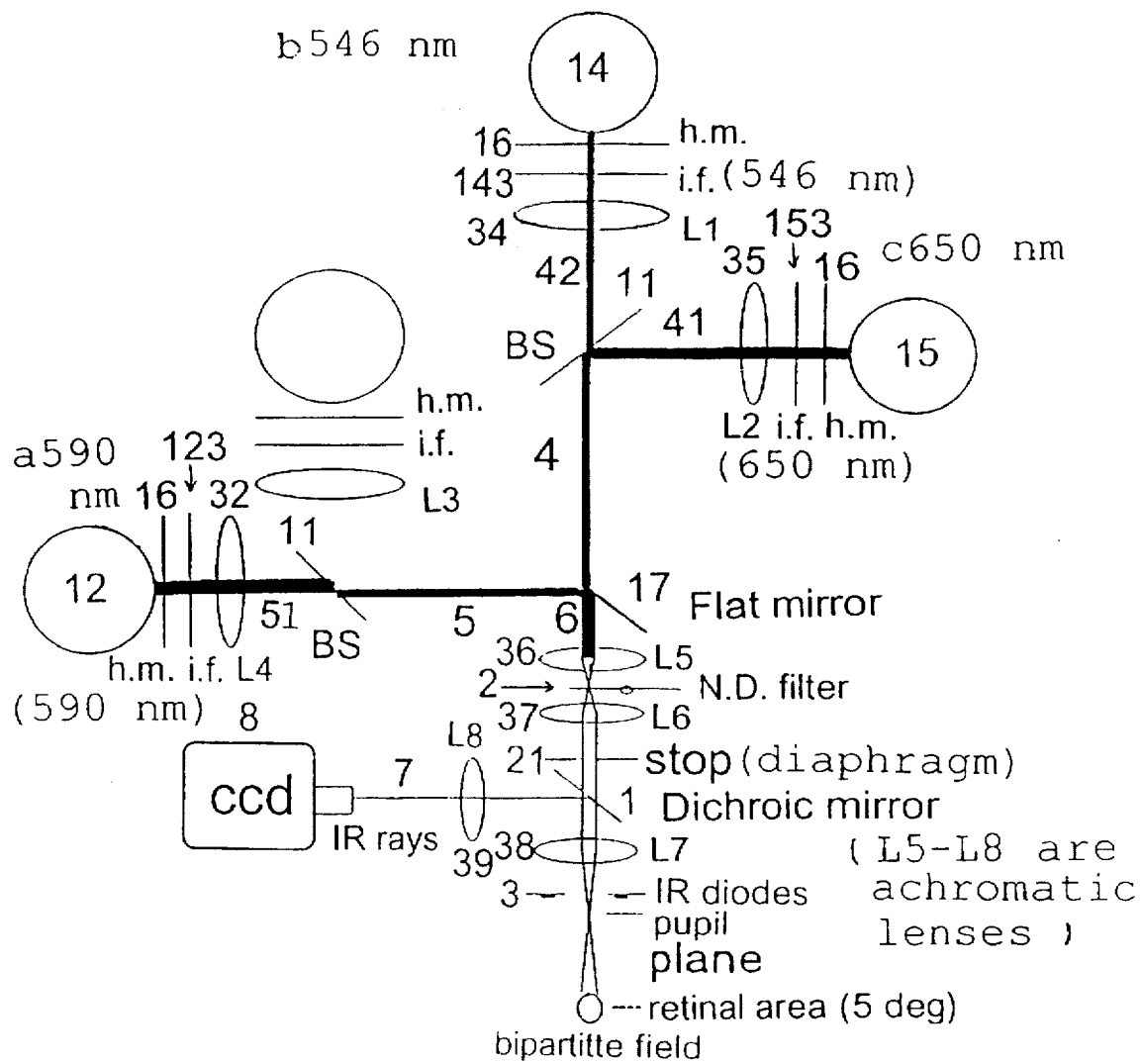
FIG. 7 is a schematic diagram showing another embodiment of a three channel anomaloscope which can generate different illuminance for test, in which, Rayleigh's match is being used.

The number of above mentioned interference filters of single wavelength used in the prudent system is seven. The purpose of these filters is to respectively adjust the light wave emitted by those illuminating light bulbs into single beam of different wavelength required. The embodiment of the present invention for Moreland's match as showing in FIG. 6 is made by adopting number of filters to adjust the light wave of four light bulbs into four single beams of different wavelength; of which, the first filter (123) adjusted the light wave of first light bulb adjacent to it into 580 mm. The second filter (133) adjusted the light wave of second bulb adjacent to it into 480 mm. The third filter (143) adjusted the light wave of the third bulb adjacent to it into 440 mm and the fourth filter adjusted the light wave of fourth bulb adjacent to it into 500 mm. The composite formula resulted in Moreland's equation is indicated below:

$$a\ 580\ nm + b\ 480\ nm = c\ 440\ nm + d\ 500\ nm.$$

The function of a hot mirror (16) to be placed between any of the illuminating lamp and filter is to reflect IR light back into lamp housing which will allow the visible light to penetrate in order to prevent the filter from damage by heat. Also, filters (123, 133, 143, 153) of specific wave length, through which a light wave of single color can be produced. At the rear of the filter placed with convex lens (32, 33, 34, 35) respectively, which have its focus positioned on the filament of halogen lamp, and a parallel light is produced. Photodiode is provided at the rear of each filter for detecting the intensity of light beam passing through this channel in order to maintain a constant value of light intensity of this two halves during the course of test.

Of these two pieces of 50/50 light splitter, the first light splitter (11) is located on the cross point of light path (52) having 580 mm wave length and light path (51) having 480 mm wave length, and its mirror plane will equally divide the right angle between this two beam into two 45 degrees to form the first mixed light beam (5). The second light splitter (11) is located on the cross point of light path (42) having 440 mm wave length and light path (41) having 500 mm wave length, and its mirror plane will equally divided the right angle between these two beams into two 45 degrees to form the second mixed light beam (4). One edge of said flat mirror (17) is set in 45 degrees at the cross point with the two mixed light beams. Part of the first mixed light beam (5) which is splitted by the edge of the flat mirror is reflected by the flat mirror and travels in parallel with the second mixed light path. This part of the first mixed light beam forms the right half of the bipartite field. Part of the second mixed light beam (4) is blocked by the edge of the flat mirror, and the rest of it will form the left half of the bipartite field. Of the so formed two half circle light beam (6), the color and brightness of the left half is maintained constant during test and the color and brightness of the right half is controlled by control circuit and computer means in order to match with the left half. The resultant color is somewhere in between pure green (such as 500 mm) and blue (such as 440 mm).

After passing through an achromatic lens (36), this two half circle light beam will focused on a non-linear circular N.D. filter (2). This N.D. filter has a maximum attenuation capability of $10^4$ times to light intensity and its focus point is controlled by a step motor. Through adjustment, this attenuation can be precisely repeated at eight positions which required to attenuating the light intensity, thus, an uniformed light intensity for test can be obtained. Achromatic lenses (36, 37) respectively at before and after side of ND filter (2) are the type of short focal lengthes, through which the two half circle light beam (6) appeared to be in the form of parallel light. The diaphragm (21) on this light path can adjust its size of diameter in order to bring the two halves of mixed light (6) to be appeared on the retina with a range from 0 to 15 degrees. The anomaloscope which can generate different illuminance for test according to the present invention designed its major targets on 2°, 5° and 10° for its range of viewing angle.

After this parallel light passed through a dichroic mirror which positioned in 45 degrees with the light path, entered into another achromatic lens (38) having a longer focus length which will bring the forementioned four light beams focused on the center of observer's pupil. Hence it will be able to make this two half circle becomes a colored circle with uniform brightness onto the observer's retina. In addition, four IR LEDs (3) are provided surrounding the transmission hole in front of observer's eye for the purpose of illuminating observer's eyeball, and the reflective IR light of the eye image was reflected by a dichroic mirror on the light path and caused the eye image being caught by a CCD camera through a biconcave lens (39). Thus, the eye image including the movement of test subject's eyeball and the alignment of pupil's position could be monitored by a B/W TV so as to achieve the best adjustment for focusing light position on the pupil as required by tester.

A method for four channel anomaloscope which can generate different illuminance for test according to the present invention to produce two half circles with uniformed brightness comprises the following steps:

(1) In order to varying color in the test half circle and to match the desired color in the reference half circle, control circuits (FIGS. 2–5) are needed to achieve the above purpose. A potential meter which is connected to the control circuits is provided for the needs of color matching.

(2) To convert the analog signal of the potential meter into digital signal by using high resolution (12 bits) A/D converter in said circuit control means.

(3) To operate the values of above digital signals through the following two equations:

$$a\ 580\ nm + b\ 480\ nm = c\ 440\ nm + d\ 500\ nm \quad (1)$$

$$0 \leq a, b, c, d \leq k$$

$$a + b = k$$

$$c + d = k \quad (2)$$

where k is a constant
obtained data a, b, c, and d: and (4) The values of above a, b are constants and the values of c, d are variables through adjusting the potential meter of control circuits means by turning or pushing buttons (or by controlling the length of time for programmly detection and control with pressing bottom).

(5) To convert the calculated values of above a, b, c, and d into analog signals in the form of voltage through four D/A converters and further transfer them into electronic servo circuit of circuit controlling device, so as to be able to unify the brightness and achieve the desired color of this two halve circles at both right and left sides.

(6) In equation (1), a pair of c,d values are usually written in ratio form c/d. This is a matching data. Generally, there are six matching data have to be collected at each retinal illuminance. The mean value of the maximum and minimum matching data of the six matching values is called midpoint. And the difference of the two extreme values is called matching range.

For Rayleigh match, we use three pieces of filters to adjust the light from three lamps into three different single light beams of different wavelengths. The first is 590 nm, the second is 650 nm and the third is 546 nm, the resultant of above three is indicated by:

$$a\ 590\ nm = b\ 650\ nm + c\ 546\ nm.$$

An idea to define the discriminative sensitivity in this color matching technique is that the midpoint value is calculated from the mean of one's highest and lowest matching data. The difference of the two matching data is the matching range. We may have an idea that the narrower the matching range the better the discriminative ability. But we have to point out that this statement must be based on having the same midpoint value when two matching ranges are compared. But it is hard to have the same midpoint values from any two sets of color matching data.

Therefore we shall build up an objective method to evaluate one's color discriminative ability. And it can be difined as following:

Color discriminative Ability(CDA)=1/(matching range×midpoint)

According to the above algorithm, the more the CDA value, the better of one's discriminative ability in color sensation.

Steps of Test

Figure 8:
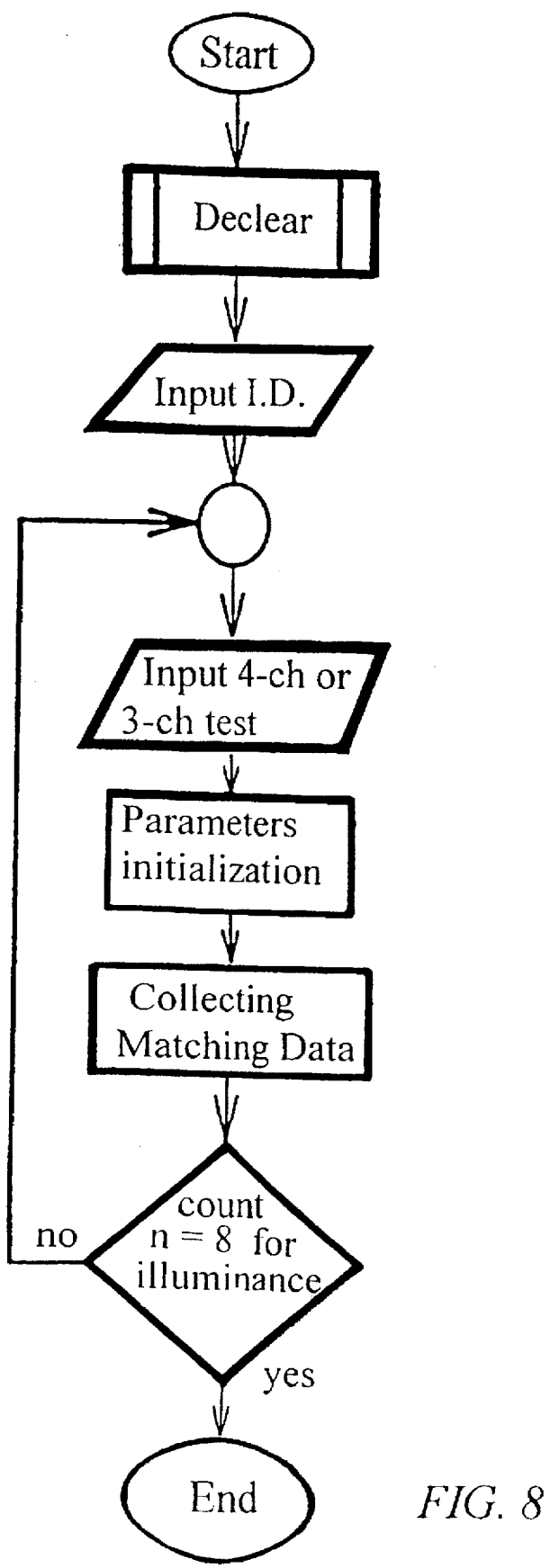
FIG. 8 is a schematic block diagram showing the control of each channel and flow chart for test operation.

There are two ways to carry-out the test by using the anomaloscope of the present invention: one is ADAPTATION and the other is TOLERANCE, the details of which is illustrated in FIG. 8—the channel control and flowchart for test.

The adaptation is to have the observer to start with low brightness. First, the test subject's eye shall have to adapt to this brightness by concentrately looked on this two half circles for at least three minutes before take action for color match. There are six matches should be made to obtain its desired criterian. Then, increase the brightness and repeat the above steps and so on, until the last high brightness test is made. The tolerance test is similar to the adaptation test, except that the adaptation to the brightness by observing the bipartite field for 3 minutes is omitted, and 2 matches start from either direction of the primary colors are required instead of 6 matches in adaptation test.

Figure 9:
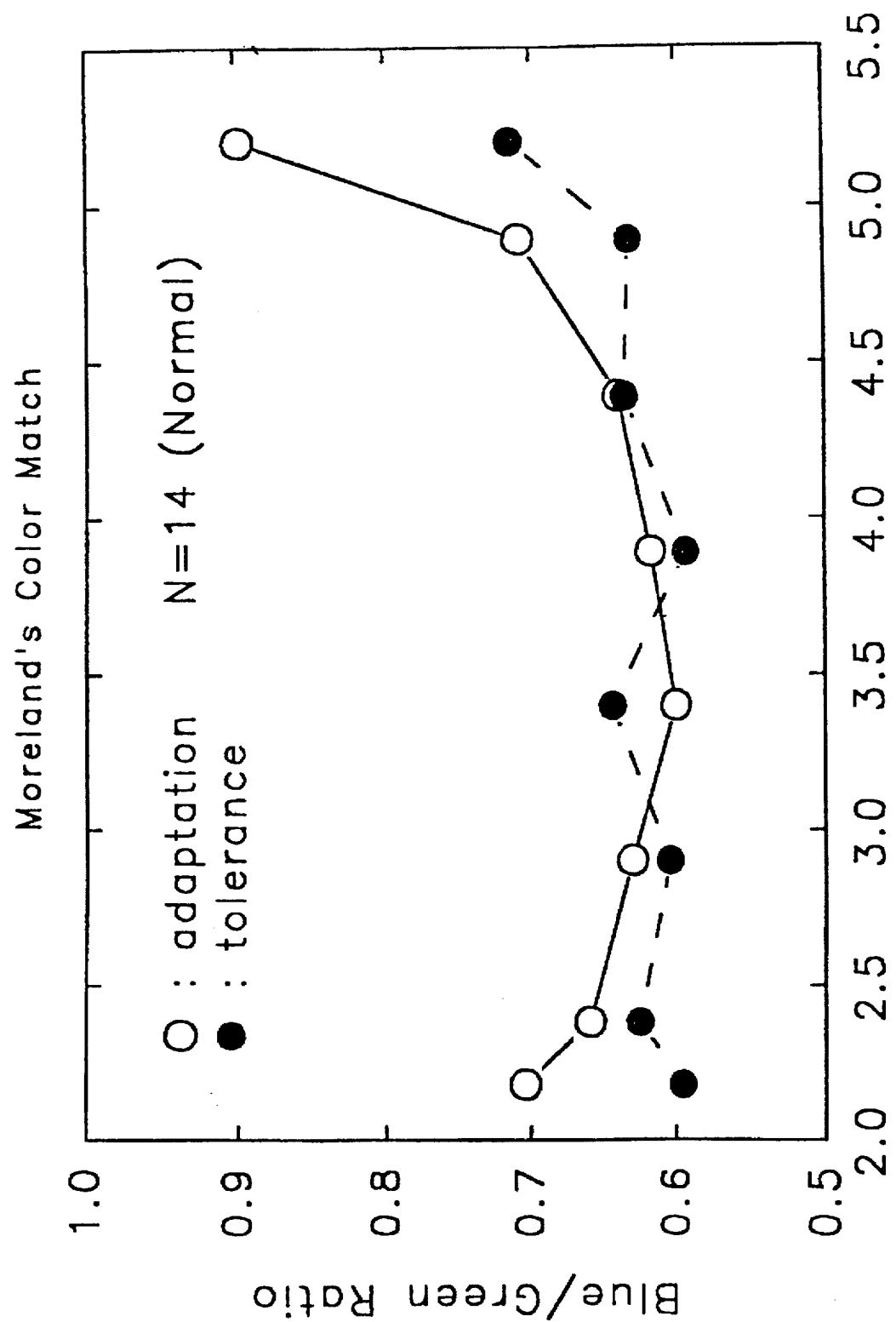
FIG. 9 is a chart illustrates the color matching v.s. retinal illuminances for a normal person with Moreland's color match.
Figure 10:
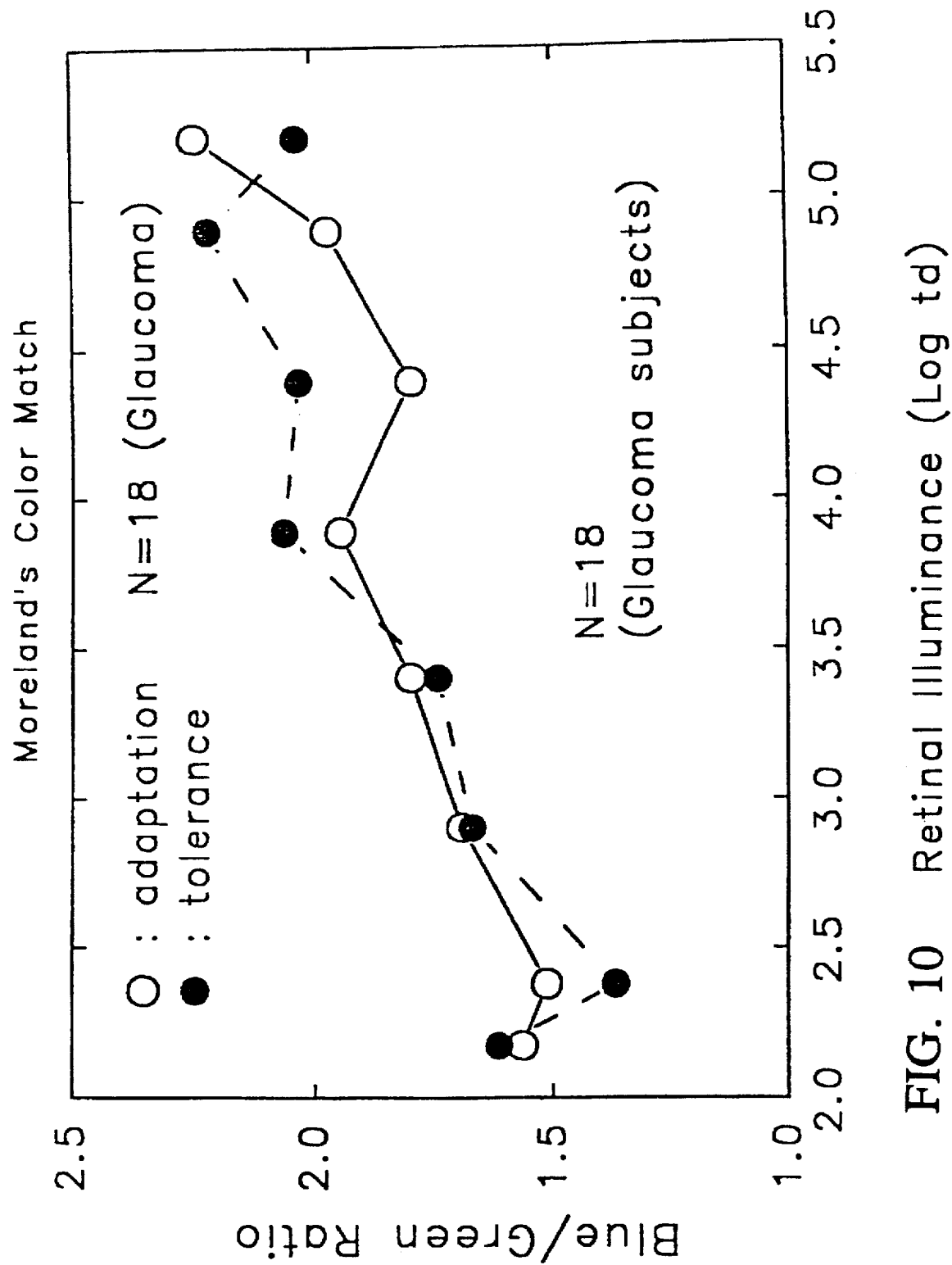
FIG. 10 is a chart illustrates the color matching v.s. retinal illuminances for a person having glaucoma with Moreland's color match.
Figure 11:
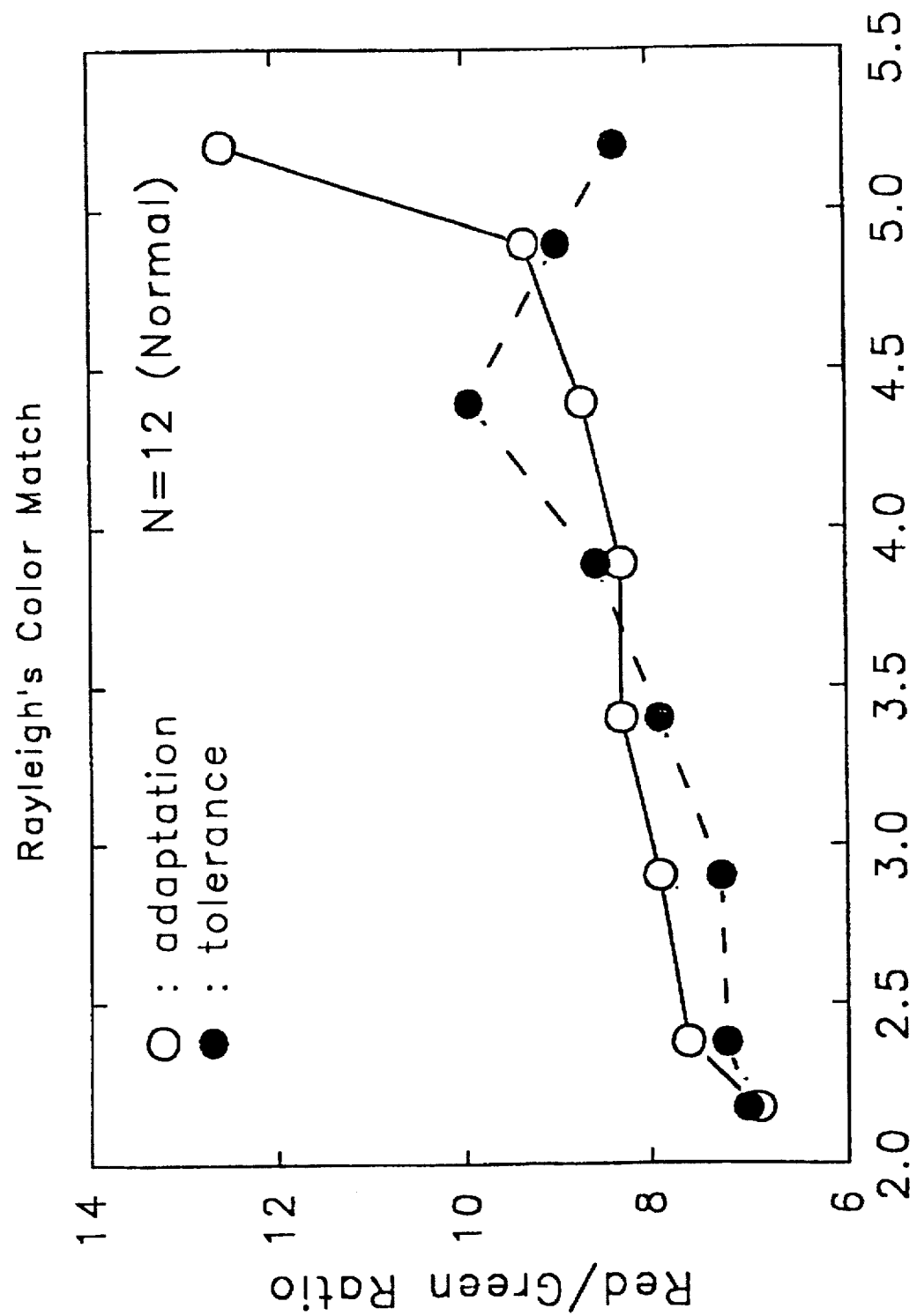
FIG. 11 is a chart illustrates the color matching v.s. retinal illuminances for a normal person with Rayleigh's color match.
Figure 12:
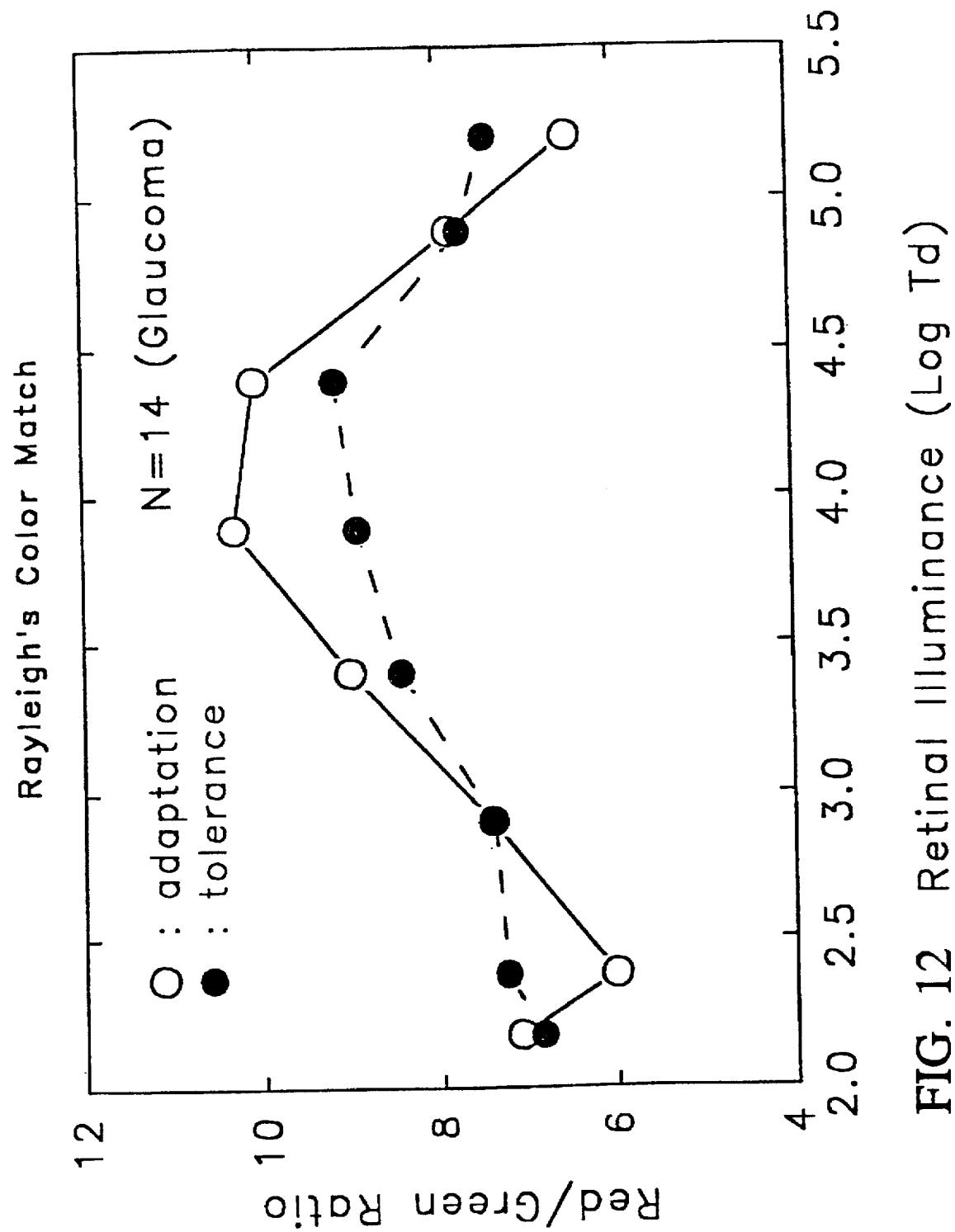
FIG. 12 is a chart illustrates the color matching v.s. retinal illuminances for a person having glaucoma with Rayleigh's color match.

Thus, we shall be able to obtain a Moreland's color match with Blue/Green Ratio as vertical axis and Retinal illuminance as horizontal axis as indicated in FIG. 9, in which, the white dots represented adaptation for a normal person and black dots represented tolerance for a normal person. The Moreland's color match for glaucoma is illustrated in FIG. 10, in which, the white dots represented adaptation and black dots represented tolerance. The same way applied for Rayleigh's match as indicated in FIG. 11 (for normal) and FIG. 12 (for glaucoma).

What is claimed is:

1. An anomaloscope for generating different illuminance for testing an eye of a subject, said anomaloscope comprising:

a housing, said housing having an interior divided by a ventilated partition plate into an upper chamber and a lower chamber, said upper chamber having a lateral side wall provided with a light transmission hole passing therethrough, said housing having a top wall with a plurality of small holes passing therethrough for heat removal, and at least one fan within said lower chamber for blowing heat out of said lower chamber;

an optical means within said upper chamber of said housing, a plurality of infrared diodes on the exterior of said housing and disposed about said transmission hole, a circuit control means connected to said optical means for controlling an operation of said optical means, and a computer with an applied software program for operating said circuit control means to accurately control said optical means;

said optical means including:

- at least one half light beam means having at least one different wavelength light source and a 50/50 light splitter mounted at a cross point of light beams from at least one different wavelength light source to form one output light beam,
- a reflector at a cross point of light beams from at least one half light beam means for producing a two halves light beam,
- a first achromatic lens for focusing the two halves light beam,
- a ND filter for attenuating the two halves light beam focused by said first achromatic lens,
- a one step motor for controlling the rotation of said ND filter,
- a second achromatic lens at a distance equal to a focus length from said ND filter,
- a shutter diaphragm for adjusting the size of diameter of the two halves light beam from said second achromatic lens,
- a dichroic mirror set at an angle of 45 degrees with a light path of the two halves light beam from said shutter diaphragm,
- a third achromatic lens for focusing the two halves light beam from said dichroic mirror onto a center of the pupil of the eye of a test subject, and said third achromatic lens passes light reflected by the pupil to said dichroic mirror,
- a fourth achromatic lens located on a light path perpendicular to the light path of the two halves light beam for receiving a reflection of said dichroic mirror of the light reflected by said pupil, and
- a CCD camera for capturing the reflection of said dichroic mirror located at a focal plane of said fourth achromatic lens; and each of said at least one different wavelength light source includes:

- a lamp housing,
- a light bulb in said lamp housing,
- a hot mirror adjacent to said light bulb, said hot mirror reflecting any infrared light emitted by said light bulb into said lamp housing,
- at least one interference filter of single wavelength for adjusting light transmitted through said hot mirror into a light beam of single wavelength, said each of at least one interference filter having a rear surface opposite said hot mirror,
- a plurality of photodiodes mounted on said rear surface of each interference filter, said plurality of photodiodes receive a strength of the light beam of single wavelength to provide negative feedback control, and
- a lens with a focal length equal to a distance between said lens and said light bulb for focusing the light beam of single wavelength.

2. The anomaloscope as claimed in claim 1, wherein the ventilated partition plate has a plurality of air holes passing therethrough.

3. The anomaloscope as claimed in claim 1, wherein there is a least one fan for each lamp housing.

4. The anomaloscope as claimed in claim 1, wherein the light bulbs are FCS 24V, 150 W projection lamp having significant brightness and numbering four.

5. The anomaloscope as claimed in claim 1, wherein a number of hot mirrors is four and a number of interference filters of single wavelength is seven.

6. The anomaloscope is claimed in claim 5, wherein one interference filter has a wavelength of 580 nm, a second interference filter has a wavelength of 480 nm, a third interference filter has a wavelength of 440 nm and a fourth interference filter has a wavelength of 500 nm.

7. The anomaloscope as claimed in claim 5, wherein a first interference filter has a wavelength of 590 nm, a second interference filter has a wavelength of 650 nm and a third interference filter has a wavelength of 546 nm.

8. The anomaloscope as claimed in claim 1, wherein a first 50/50 light splitter is located on the cross point of a light beam having a wavelength of 580 nm and a light beam having a wavelength of 480 nm, and a mirror plane of at least one 50/50 light splitter will equally divide the right angle between these two light beams into two 45 degrees to form an output light beam;

a second 50/50 light splitter is located on the cross point of a light beam having a wavelength of 440 nm and a light beam having a wave length of 500 nm.

9. The anomaloscope as claimed in claim 1, wherein said reflector having an one end located at the cross point of a first output light beam with a plane at a position of 45 degrees from the first output light beam facing towards a direction to a second output light beam, whereby a right half of the first output light beam shall be blocked and only a left half of the first output light beam will pass through the light transmission hole on the housing to form a left half of the two halves light beam.

10. The anomaloscope claimed as claim 1, wherein the two halves light beam formed by said reflector has a left half having a constant color and brightness during testing and a right half being controlled by said circuit control means and said computer in order to match the right half with the left half with the brightness of the right half being identical with the left halve and the right half color being between pure green (500 nm) and pure blue (440 nm).

11. The anomaloscope as claimed in claim 1, wherein the two halves light beam formed by said reflector has a left half having a constant color and brightness during testing and a right half being controlled by said circuit control means and said computer in order to make the right half completely identical with the left half based on Rayleigh's match whereby the right half color is between yellow green (546 nm) and red (650 nm).

12. The anomaloscope as claimed in claim 1, wherein said shutter diaphragm diameter is adjustable both manually and automatically by said circuit control means.

13. The anomaloscope as claimed in claim 1, wherein said dichroic mirror is tilted at a 45 degree angle in a direction of left-up and right-down, said dichroic mirror allows visible light to penetrate and reflects IR light.

14. The anomaloscope as claimed in claim 1, wherein four light emitting diodes each having a wavelength of around 950 nm located around said light transmission hole on said housing at an equal distance and form a right angle with the center of the transmission hole; and said fourth achromatic lens forms a confocal plane with the pupil plane.

15. The anomaloscope as claimed in claim 1, wherein said at least one interference filter has a wavelength of between 400 nm and 700 nm.

16. The anomaloscope as claimed in claim 1, wherein a three channel anomaloscope can be made by having three different wavelength light sources.

17. An anomaloscope for generating different illuminance for testing an eye of a subject, said anomaloscope comprising:

a housing, said housing having an interior divided by a ventilated partition plate into an upper chamber and a lower chamber, said upper chamber having a lateral side wall provided with a light transmission hole passing therethrough, said housing having a top wall with a plurality of small holes passing therethrough for heat removal, and at least one fan within said lower chamber for blowing heat out of said lower chamber;

an optical means with said upper chamber of said housing, a plurality of light emitting diodes on the exterior of said housing and disposed about said transmission hole for illuminating the eye of a subject, a circuit control means connected to said optical means for controlling an operation of said optical means, and a computer with an applied software program for operating said circuit control means to accurately control said optical means;

said optical means including:

at least one half light beam means having at least one different wavelength source and a 50/50 light splitter mounted at a cross point of light beams from at least one different wavelength source to form one output light beam, a reflector at a cross point of light beam from at least one half light beam means for producing a two halves light beam, a pair of achromatic lenses for focusing the two halves light beam from said reflector into parallel light beams, a ND filter for attenuating the parallel light beams focused by said pair of achromatic lenses, a shutter diaphragm for adjusting the size of diameter of the parallel light beams from said ND filter, a dichroic mirror set an angle of 45 degrees with a light path of the parallel beams, said dichroic mirror allows visible light from said shutter diaphragm to pass through and reflects IR light, a third achromatic lens for focusing the parallel light beams from said dichroic mirror on a certain point in space, and said third achromatic lens passes light reflected by said pupil to said dichroic mirror, a fourth achromatic lens located on a light path perpendicular to the light path of the parallel light beams for receiving a reflection of said dichroic mirror of the light reflected by the pupil and focusing the reflection, a CCD camera for capturing the reflection of said dichroic mirror located at a focal plane of said fourth achromatic lens, and a television for monitoring the test and reproducing the reflection captured by said CCD camera; and each of said at least one different wavelength light source includes:

a lamp housing, a light bulb in said lamp housing, a hot mirror adjacent to said light bulb, said hot mirror reflecting an infrared light emitted by said light bulb into said lamp housing, at least one interference filter of single wavelength for adjusting light transmitted through said hot mirror into a light beam of single wavelength, said each of at least one interference filter having a rear surface opposite said hot mirror, a plurality of photodiodes mounted on said rear surface of each interference filter, said plurality of photodiodes receive a strength of the light beam of single wavelength to provide negative feedback control, and a lens with a focal length equal to a distance between said lens and said light bulb for focusing the light beam of single wavelength.

* * * * *